United States Patent
Haswell et al.

(10) Patent No.: US 6,989,090 B2
(45) Date of Patent: Jan. 24, 2006

(54) METHOD TO MONITOR CHEMICAL REACTIONS IN A MICRO-REACTOR BY MEASURING AN ELECTRICAL CURRENT

(75) Inventors: Stephen J. Haswell, Cottingham (GB); Paul D. I. Fletcher, Hull (GB); Xunli Zhang, Hull (GB)

(73) Assignee: Micro Chemical Systems Limited, Hull (GB)

( * ) Notice: Subject to any disclaimer, the term of this patent is extended or adjusted under 35 U.S.C. 154(b) by 172 days.

(21) Appl. No.: 10/210,868

(22) Filed: Aug. 2, 2002

(65) Prior Publication Data

US 2003/0047454 A1   Mar. 13, 2003

(30) Foreign Application Priority Data

Aug. 10, 2001   (GB) .................................... 0119798

(51) Int. Cl.
*G01N 27/26* (2006.01)

(52) U.S. Cl. .................... 205/793.5; 204/450

(58) Field of Classification Search ................ 204/400, 204/409, 452, 454, 600, 601, 602; 205/793.5, 205/775; 324/691, 693; 422/82.01–82.02; 429/70
See application file for complete search history.

(56) References Cited

U.S. PATENT DOCUMENTS

| | | | |
|---|---|---|---|
| 2,525,754 A * | 10/1950 | Albrecht | 324/448 |
| 3,912,613 A | 10/1975 | Heuser | |
| 4,794,089 A * | 12/1988 | Mroczkowski et al. | 436/501 |
| 4,876,205 A | 10/1989 | Green et al. | |
| 5,194,133 A * | 3/1993 | Clark et al. | 204/608 |
| 5,262,127 A | 11/1993 | Wise et al. | |
| 5,298,139 A * | 3/1994 | Huang et al. | 204/603 |
| 5,637,469 A * | 6/1997 | Wilding et al. | 435/7.21 |
| 5,853,668 A * | 12/1998 | Begg et al. | 422/82.02 |
| 5,889,200 A * | 3/1999 | Centers et al. | 73/53.01 |
| 5,942,443 A * | 8/1999 | Parce et al. | 436/514 |
| 5,965,410 A * | 10/1999 | Chow et al. | 435/91.2 |
| 6,149,787 A | 11/2000 | Chow et al. | |
| 6,174,675 B1 * | 1/2001 | Chow et al. | 435/6 |
| 6,729,352 B2 * | 5/2004 | O'Connor et al. | 137/827 |
| 2002/0072054 A1 | 6/2002 | Miles et al. | |

FOREIGN PATENT DOCUMENTS

| | | |
|---|---|---|
| EP | 0 616 218 A1 | 9/1994 |
| JP | 61090047 A | 10/1984 |
| WO | WO 90/11291 | 10/1990 |
| WO | WO 00/42424 | 7/2000 |

* cited by examiner

*Primary Examiner*—Kaj K. Olsen
*Assistant Examiner*—R. Michelle Vestal
(74) *Attorney, Agent, or Firm*—Leydig, Voit & Mayer, Ltd.

(57) ABSTRACT

A reaction is performed in a micro-reactor (10), voltages being applied by a power supply (12), under the control of a processor (14), so as to cause the reagents to move and react in the channels (24',30',32',34',36') of the micro-reactor (10). The power supply (12) also measures currents in the channels and relays this information to the processor (14). The currents are used to monitor progress of the reaction.

13 Claims, 2 Drawing Sheets

METHOD TO MONITOR CHEMICAL REACTIONS IN A MICRO-REACTOR BY MEASURING AN ELECTRICAL CURRENT

The invention relates to methods and apparatus for monitoring chemical reactions.

It is known to perform chemical reactions in micro-reactors. A micro-reactor generally has a plurality of interconnected channels having widths in the region of 10 $\mu$m to 500 $\mu$m. Micro-reactors also generally have a plurality of reservoirs which communicate with the channels. Reagents for a reaction can be placed into respective reservoirs. Voltages are then applied between the reservoirs so as to cause the reagents to move and mix in the channels.

According to a first aspect of the invention there is provided a method of monitoring a chemical reaction comprising, performing a chemical reaction in a fluid, the reaction altering the conductivity of the fluid, applying a voltage so as to generate a current in the fluid, measuring the current, and using the current measurement to monitor the reaction.

According to a second aspect of the invention there is provided an apparatus for monitoring a chemical reaction, the apparatus comprising a device having at least one channel for performing a chemical reaction in a fluid therein, a power source for applying a voltage to fluid in the at least one channel, and means for measuring a current passing through the fluid in the channel.

The following is a more detailed description of an embodiment of the invention, by way of example, reference being made to the appended schematic drawings in which.

Figure 1:
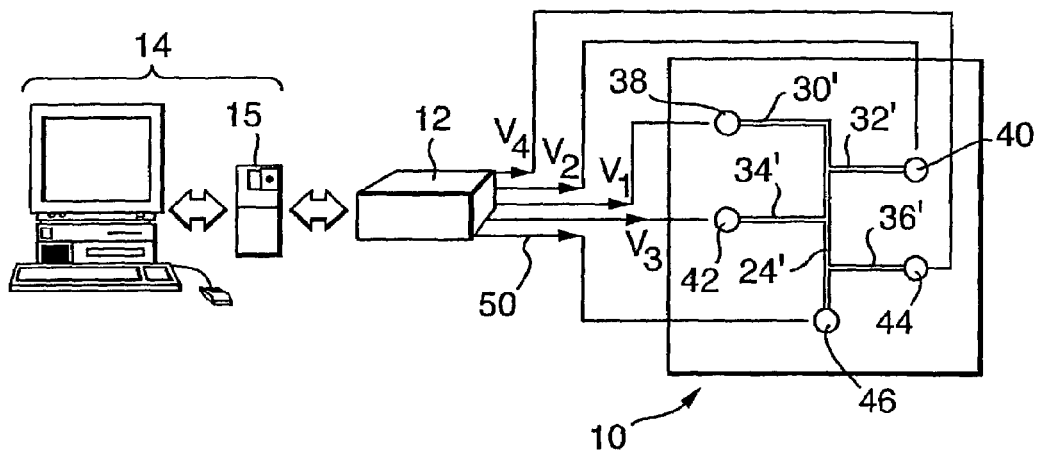
FIG. 1 shows components of an apparatus suitable for monitoring a chemical reaction in a micro-reactor.

As shown in FIG. 1, the apparatus comprises a micro-reactor 10, a power supply 12 and a processor 14.

Figure 2:
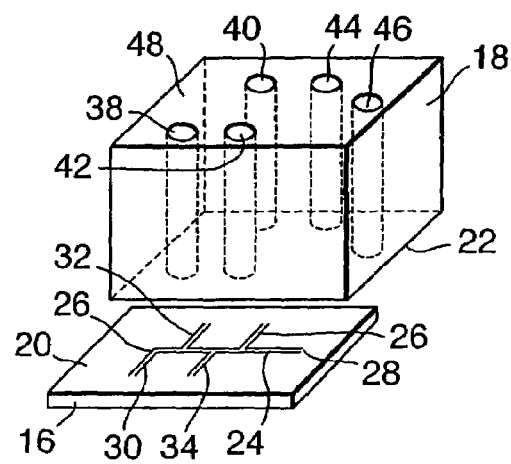
FIG. 2 shows a stage in the production of a micro-reactor that forms part of the apparatus of FIG. 1.

As indicated in FIG. 2, the micro-reactor 10 is formed from a base plate 16 and an upper block 18, both of which are of glass. The base plate 16 has an upper surface 20 and the upper block 18 has a lower surface 22. The upper surface 20 and the lower surface 22 are bonded to one another—these surfaces 20,22 being shown spaced from one another in FIG. 2 as FIG. 2 shows a stage in the manufacture of the micro-reactor 10.

The micro-reactor 10 has five interconnected channels that extend between the base plate 16 and the upper block 18. The channels correspond to five interconnected grooves that were etched into the upper surface 20 of the base plate 16 before the base plate 16 and the upper block 18 were bonded together. As shown in FIG. 2, before bonding of the base plate 16 and the upper block 18, the upper surface 20 was provided with a main groove 24 having first and second ends 26,28 and first, second, third and fourth side grooves extending outwardly from and perpendicularly to the main groove 24. Starting from the first end 26 of the main groove 24, the first side groove 30 extends from the first end 26 to a first side of the main groove 24. The second side groove 32 extends to a second side of the main groove 24, and from a position approximately one quarter of the distance from the first end 26 to the second end 28 of the main groove 24. The third side groove 34 extends to the first side of the main groove 24, and from a position approximately mid-way between the first and second ends 26,28 of the main groove 24. The fourth side groove 36 extends to the second side of the main groove 24, and from a position approximately three quarters of the distance from the first end 26 to the second end 28 of the main groove 24. Each of the side grooves 30,32,34,36 opens into the main groove 24.

The main groove 24 and the side grooves 30,32,34,36 were etched into the upper surface 20 in a known manner. The main groove 24 and the four side grooves 30,32,34,36 had respective widths of 300 $\mu$m and respective depths of 100 $\mu$m.

After bonding the upper surface 20 of the base plate 16 to the lower surface 22 of the upper block 18 (which is achieved using known thermal bonding techniques), the lower surface 22 closes the grooves 24,30,32,34,36 so as to form the interconnected channels which, of course, have the same configuration as the grooves. The five channels will be referred to below as the main channel 24', the first side channel 30', the second side channel 32', the third side channel 34', and the fourth side channel 36'.

The micro-reactor 10 also has first, second, third, fourth and fifth reservoirs 38,40,42,44,46. Each reservoir 38,40,42,44,46 is formed by a 2 mm diameter cylindrical hole that extends through the upper block 18 from the lower surface 22 to an upper surface 48.

The first reservoir 38 lies above and communicates with the outer end of the first side channel 30', the second reservoir 40 lies above and communicates with the outer end of the second side channel 32', the third reservoir 42 lies above and communicates with the outer end of the third side channel 34', the fourth reservoir 44 lies above and communicates with the outer end of the fourth side channel 36' and finally, the fifth reservoir 46 lies above and communicates with the second end 28 of the main channel 24'.

Respective platinum wire electrodes (not shown—0.26 mm in diameter) are insertable in each of the first to fifth reservoirs 38,40,42,44,46.

The power supply 12 has four high voltage channels ($V_1$–$V_4$ in FIG. 1) which can independently supply voltages in the range of zero to ±1,000V relative to a common ground 50. Each of the four channels ($V_1$–$V_4$) can be electrically connected to a respective one of the platinum electrodes (not shown) in the first, second, third and fourth reservoirs 38,40,42,44. The common ground 50 is electrically connected to the platinum electrode in the fifth reservoir 46. This is shown schematically in FIG. 1.

The power supply 12 also has four output signal channels for outputting respective signals indicative of the voltages, relative to the common ground, of the high voltage channels $V_1$–$V_4$.

Additionally, the power supply 12 includes a current sensor which is adapted for measuring currents and has four output signal channels that output respective signals indicative of currents that run, during operation, in the channels of the micro-reactor 10. For example, when the four high voltage channels $V_1$–$V_4$ are connected, respectively, to the first, second, third and fourth reservoirs 38,40,42,44, and the common ground is connected to the fifth reservoir 46, and when the channels are filled with conductive fluid, a first output signal channel indicates the current running between the first reservoir 38 and the fifth reservoir 46, a second output channel indicates current running between the second reservoir 40 and the fifth reservoir 46, a third output channel indicates current running between the third reservoir 42 and the fifth reservoir 46, and finally, a fourth output channel indicates current running between the fourth reservoir 44 and the fifth reservoir 46.

Finally, the power supply 12 has four input signal channels. Each one of the input channels receives signals for controlling the voltage applied by a respective one of the four high voltage channels $V_1$–$V_4$.

The power supply 12 has a setting and actual voltage accuracy of ±0.1%. The voltage stability is 0.5% over 1 hour. Finally, the response time is 90% voltage changing within 100 µs.

The processor 14 comprises a standard PC on which is run a programme that allows the high voltages that are applied to the first, second, third and fourth reservoirs 38,40,42,44 to be controlled individually over time and that monitors the currents that run in the channels of the micro-reactor 10. The programme will be referred to as the control programme. The processor 14 is also provided with two interface boards 15 that allow the processor 14 to communicate with the power supply 12. The two interface boards are available from National Instruments under the model nos. PCI-6031E and PCI-6703.

The processor 14, together with the interface boards 15, provide the four signals to the four input signal channels of the power supply 12 (which in turn control the high voltages applied by the voltage channels $V_1$–$V_4$. The arrangement is such that the voltage of each high voltage channel $V_1$–$V_4$ can be raised and lowered individually, over time, independently of the voltages of the other high voltage channels $V_1$–$V_4$.

The processor 14, via the interface boards 15, also receives the four signals from the power supply 12 which indicate the magnitudes of the voltages applied to the four high voltage channels $V_1$–$V_4$. In this way, the processor 14 is able to monitor the actual voltages that are applied.

The processor 14 also receives, via the interface boards 15, the four signals from the current sensor of the power supply 12 that indicate, respectively, the currents running between the first, second, third and fourth reservoirs 38,40, 42,44, and the fifth reservoir 46. In this way, the processor 14 is able to monitor the currents running in the channels of the micro-reactor 10.

The control programme is able to acquire the input data, that is to say the four input signals that relate to the voltages applied and the four input signals that indicate the currents running in the micro-reactor 10, at a rate of 10 times each second. This data is displayed and is also written to a spread sheet file for future analysis.

The control programme is able to control the voltages applied to the micro-reactor 10, and receive the input data from the power supply 12, automatically.

Use of the apparatus described above, to perform a chemical reaction and to monitor progress of the chemical reaction, will now be described.

The first step is to calibrate the apparatus so as to determine the residual currents. The residual currents are the currents that are recorded by the apparatus when the processor 14 and the power supply 12 are set to apply voltages in the absence of any external load—that is to say when the micro-reactor 10 is not connected to the power supply 12. This is done by recording the residual currents (in the absence of any external load) as the set voltage is increased from zero to 1,000V in 50V steps. In the apparatus described above this operation reveals a straight line calibration curve extending from 0 µA at 0V to 100 µA at 1,000V.

The results of the calibration step are stored in the processor 14, in the form of a look-up table, so that for any voltage applied by the power supply 12 to the micro-reactor 10 a corresponding residual current can be obtained from the look-up table. The control programme is set up so that, when a voltage is applied between any one of the first, second, third and fourth reservoirs 38,40,42,44, and the fifth reservoir 46, the appropriate residual current, corresponding to the applied voltage, is subtracted from the apparent current running between those two reservoirs.

The apparatus can now be used to perform and monitor a chemical reaction.

Figure 3:
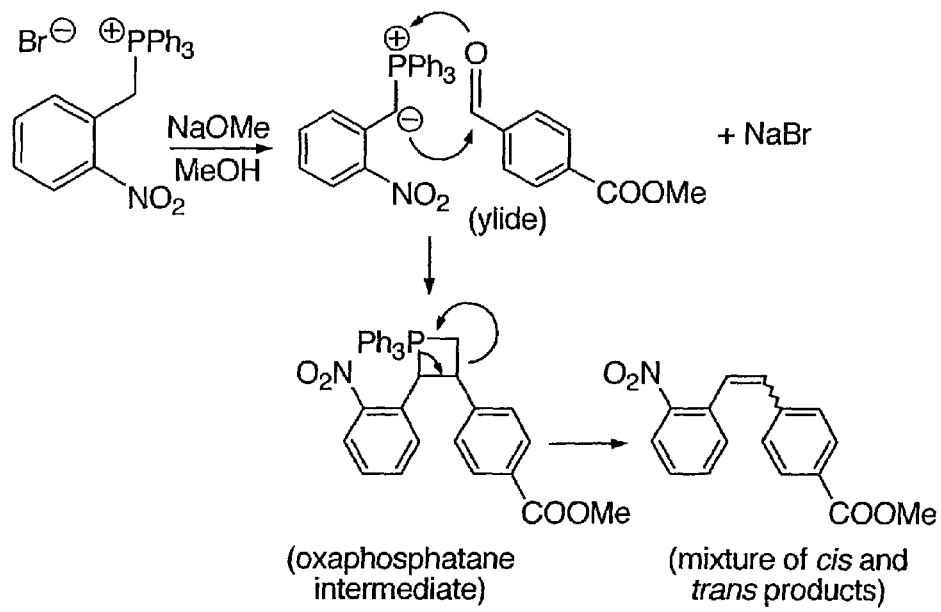
FIG. 3 shows a two step Wittig reaction.

By way of example, use of the apparatus to perform and monitor a Wittig reaction will be described. The exemplary Wittig reaction is shown schematically in FIG. 3. As shown in FIG. 3, 2-nitrobenzyltriphenyl-phosphonium bromide was reacted with sodium methoxide to yield a coloured intermediate (ylide) plus sodium bromide. The ylide reacted with methyl 4-formylbenzoate via an oxaphosphatane intermediate to yield a mixture of cis and trans products having an alkene bond. The solvent was degassed methanol.

A solution of 2-nitrobenzyltriphenyl-phosphonium bromide (50 µL, 0.01 M) in dry degassed methanol was added to the first reservoir 38. Methyl 4-formylbenzoate (50 µL, 0.01 M) was premixed with sodium methoxide (0.015 M) and 50 µL of the premixed solution was introduced into the second reservoir 40. Dry degassed methanol was introduced into the fifth reservoir 46. Platinum electrodes were inserted into the liquids in the first, second and fifth reservoirs 38,40,46 (and no electrodes were present in the third and fourth reservoirs 42,44).

The processor 14 was programmed so that the power supply 12 applied a voltage of +700V to the first reservoir 38 and a voltage of 650V to the second reservoir 40, relative to the fifth reservoir 46 which was connected to the common ground 50.

The applied voltages caused the 2-nitrobenzyltriphenyl-phosphonium bromide to move from the first reservoir 38 along the first side channel 30' to the main channel 24', along the main channel 24' to the fifth reservoir 46. Additionally, the methyl 4-formylbenzoate and the sodium methoxide were moved, by the voltages, from the second reservoir 40 along the second side channel 32' to the main channel 24', and along the main channel 24' to the fifth reservoir 46. The reagents met and reacted, as shown in FIG. 3, in the main channel 24'. The movement of the reagents was caused by movement of the liquids by electroosmotic forces.

Figure 4:
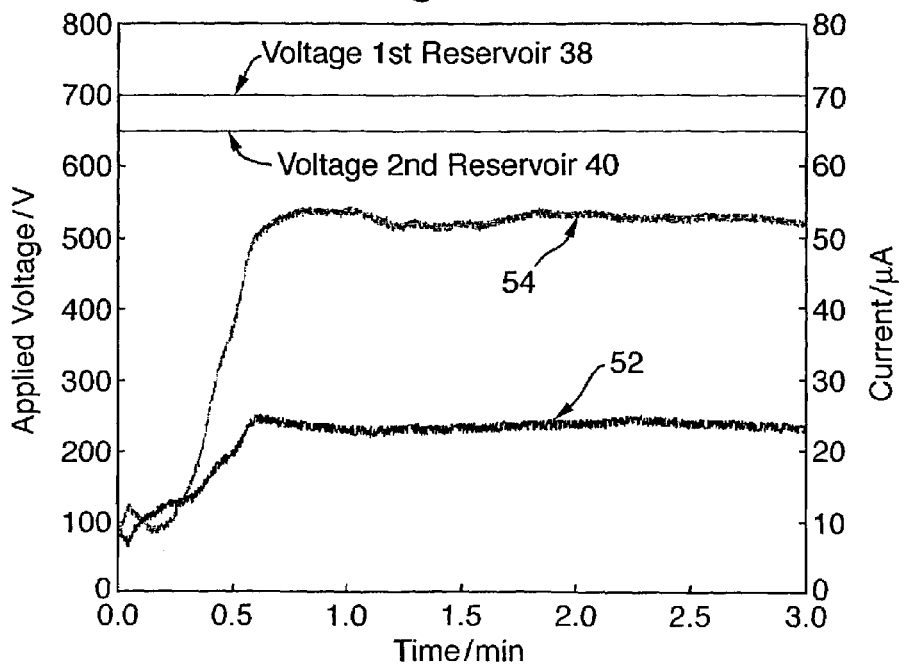
FIG. 4 shows voltage and current measurements in the apparatus of FIG. 1 when used to perform the Wittig reaction shown in FIG. 3.

During the course of the reaction, the apparatus was used to monitor the currents running between the first reservoir 38 and the fifth reservoir 46, and also between the second reservoir 40 and the fifth reservoir 46. The voltages applied to the first and second reservoirs 38,40, and the currents running between these reservoirs and the fifth reservoir 46, are shown, over time, in FIG. 4. In FIG. 4, the line 52 shows the current running between the first reservoir 38 and the fifth reservoir 46, and the line 54 shows the current running between the second reservoir 40 and the fifth reservoir 46. FIG. 4 shows that the currents increased (while the voltages remained constant) within a time period of 40 seconds after the voltages were first applied.

The increase in the measured currents corresponds to the production of sodium bromide in the reaction, as shown in FIG. 3. The sodium bromide produced ionises and this increases the conductivity of the solutions in the channels of the micro-reactor 10. Accordingly, as the voltages applied remain constant, the currents increase. Hence, the results indicate that the first stage in the reaction, the reaction of 2-nitrobenzyltriphenyl-phosphonium bromide with sodium methoxide to give the ylide and sodium bromide, was complete after 40 seconds.

It will be appreciated that the method described above may be modified in very many ways.

Firstly, the method is amenable to monitor any reaction in which the conductivity of the reaction mixture increases or decreases as the reaction progresses. A change in the conductivity of the reaction mixture might result, for example, if the reaction involves generation or removal of an ionised species. A change in conductivity may also result, for example, if there is both generation and removal of ionised species, if there is a net change in the ionic content. Change in conductivity may involve generation and/or removal of both positively and/or negatively charged species.

Additionally, the method is not limited to use of a micro-reactor having the channel geometry described above. Micro-reactors having any channel geometry may be used—the channel geometry being chosen in view of the chemical reaction desired to be performed. Indeed, the method is not limited to the performance and monitoring of chemical reactions in micro-reactors. Reactions may be performed and currents measured in any suitable apparatus. Where micro-reactors are used, the channels preferably have maximum cross-sectional dimensions in the range 10 $\mu$m to 500 $\mu$m.

Clearly, increases and decreases in currents that are measured will be interpreted according to the nature of the reaction that is being performed.

Although the exemplary method described above monitors a reaction that occurs in a liquid, the method may also be used to monitor reactions in conductive gases.

In the detailed example discussed above, the reagents moved through the channels in response to electroosmotic forces generated by the application of the voltages. This controlled the reaction as it caused and controlled the bringing together of the reagents for reaction. Monitoring may also be performed while reagents and/or products move due to electrophoresis or combinations of electroosmosis and electrophoresis. (Electroosmosis and electrophoresis are both examples of electrokinetic force.) Movement of reagents and products by electrokinetic forces is well known in the field of micro-reactors, and is commonly used to control reactions by bringing reagents together, removing products etc. While such movement (and consequent control) is not essential to the current invention, it is preferable that the voltage or voltages used to generate the current or currents is/are also used to control the reactions of the current invention by electrokinetic movement of reagents and/or products.

In the example described above, the voltages applied caused movement of the reagents and this controlled the reaction, by controlling mixing. Although it is preferable for the voltages to control reaction by movement of the reagents movement is not essential.

It is preferred, as for the reaction described above, that the reaction is not thermodynamically dependent on the current. That is to say that an electrical current is not required, thermodynamically, for performance of the reaction. Of course, the reaction may be dependent on the voltage or voltages applied, for example, to move the reagents together, for reaction, by generation of electrokinetic force.

In the detailed example described above, the applied voltages remain constant. However, this need not be the case. Each voltage may be, for example, increased and/or decreased, whether stepwise, smoothly, cyclicly or in any other way. Changes in voltage may be used, for example, to control movement of reagents by electrokinetic force.

We claim:

1. A method of monitoring a chemical reaction comprising, performing a chemical reaction involving a chemical in a liquid, the reaction altering the conductivity of the liquid, applying a voltage so as to generate a current in the liquid, measuring the current, and using the current measurement to monitor the reaction, and wherein the applied voltage causes electrokinetic movement of the chemical, the electrokinetic movement comprising electroosmotic movement of the liquid.

2. A method according to claim 1, wherein said electrokinetic movement of the chemical includes electrophoretic movement of the chemical.

3. A method according to claim 1, wherein said electrokinetic movement controls the reaction.

4. A method according to claim 3, wherein the chemical is a reagent in the reaction and said electrokinetic movement brings together the reagent with another reagent.

5. A method according to claim 1, wherein the reaction is thermodynamically independent of the current.

6. A method according to claim 1, wherein the reaction is performed in one or more channels in an apparatus, the apparatus having a first member with one or more grooves and a second member with a surface, the surface closing the one or more grooves to form the one or more channels.

7. A method according to claim 6, wherein the or each channel has a maximum cross-sectional dimension in the range of 10 $\mu$m to 500 $\mu$m.

8. A method according to claim 1, wherein the reaction is performed in one or more channels, the or each channel having a maximum cross-sectional dimension in the range of 10 $\mu$m to 500 $\mu$m.

9. A method according to claim 6, wherein said movement is movement along said one or more channels.

10. A method according to claim 8, wherein said movement is movement along said one or more channels.

11. A method according to claim 1, wherein the reaction involves the generation or removal of an ionised chemical causing or contributing to said altering the conductivity of the fluid.

12. A method according to claim 1, wherein the voltage applied is varied under the control of a processor.

13. A method according to claim 12, wherein the processor varies the voltage dependent on the current measurement.

* * * * *